United States Patent
Fuhrer et al.

(10) Patent No.: US 9,937,060 B2
(45) Date of Patent: Apr. 10, 2018

(54) PROSTHESIS HOLDER AND APPLICATION THEREOF

(71) Applicant: SPINEART SA, Meyrin, Geneve (CH)

(72) Inventors: Christophe Fuhrer, Valliere (FR); Jerome Levieux, Versoix (CH)

(73) Assignee: SPINEART SA, Meyrin, Geneve (CH)

( * ) Notice: Subject to any disclaimer, the term of this patent is extended or adjusted under 35 U.S.C. 154(b) by 395 days.

(21) Appl. No.: 14/704,306

(22) Filed: May 5, 2015

(65) Prior Publication Data

US 2015/0245924 A1    Sep. 3, 2015

Related U.S. Application Data

(62) Division of application No. 12/515,787, filed as application No. PCT/FR2007/052374 on Nov. 21, 2007, now abandoned.

(51) Int. Cl.
| | | |
|---|---|---|
| *A61F 2/46* | (2006.01) | |
| *A61F 2/44* | (2006.01) | |
| *A61F 2/00* | (2006.01) | |
| *A61F 2/30* | (2006.01) | |

(52) U.S. Cl.
CPC ............ *A61F 2/4611* (2013.01); *A61F 2/442* (2013.01); *A61F 2/0095* (2013.01); *A61F 2/4425* (2013.01); *A61F 2002/305* (2013.01); *A61F 2002/3082* (2013.01); *A61F 2002/30131* (2013.01); *A61F 2002/30649* (2013.01); *A61F 2002/30841* (2013.01); *A61F 2002/30904* (2013.01); *A61F 2002/4624* (2013.01); *A61F 2220/0025* (2013.01); *A61F 2230/0013* (2013.01)

(58) Field of Classification Search
CPC .......... A61F 2/44; A61F 2/442; A61F 2/4425; A61F 2/4611; A61F 2002/443; A61F 2002/4624; A61F 2002/4679
USPC ..................................... 606/99, 100
See application file for complete search history.

(56) References Cited

U.S. PATENT DOCUMENTS

| | | |
|---|---|---|
| 5,683,464 A | 11/1997 | Wagner et al. |
| 6,267,763 B1 | 7/2001 | Castro |
| 6,451,054 B1 | 9/2002 | Stevens |

(Continued)

FOREIGN PATENT DOCUMENTS

WO    2006016384    2/2006

OTHER PUBLICATIONS

International Search Report dated May 8, 2008, from corresponding PCT application.

*Primary Examiner* — Eric S Gibson

(74) *Attorney, Agent, or Firm* — Young & Thompson

(57) ABSTRACT

Prosthesis holder (1) made of a radiolucent material for a disc prosthesis (2) constituted by at least two parts which are mobile in relation to each another, including, on one side an element (9) for coupling to a sleeve and on the other side, an element for reversible coupling to a disc prosthesis, the reversible coupling element is arranged in order to allow decoupling, by simple traction exerted perpendicularly to a spinal column when the disc prosthesis has been correctly impacted between two vertebrae and the retention force of the reversible coupling element on the disc prosthesis is adjusted so as not to allow decoupling by simple traction when the disc prosthesis has not been correctly impacted, and an assembly including a prosthesis holder and a disc prosthesis.

16 Claims, 2 Drawing Sheets

(56) References Cited

U.S. PATENT DOCUMENTS

| | | | | |
|---|---|---|---|---|
| 7,708,778 | B2* | 5/2010 | Gordon | A61B 17/7005 623/17.15 |
| 7,803,162 | B2* | 9/2010 | Marnay | A61F 2/4425 606/99 |
| 7,981,116 | B2 | 7/2011 | Reeder, Jr. et al. | |
| 8,328,851 | B2* | 12/2012 | Curran | A61F 2/4425 606/279 |
| 8,349,017 | B2* | 1/2013 | Marnay | A61F 2/4425 606/86 A |
| 2005/0021042 | A1* | 1/2005 | Marnay | A61F 2/4425 606/99 |
| 2005/0033305 | A1* | 2/2005 | Schultz | A61F 2/4425 606/99 |
| 2005/0113926 | A1 | 5/2005 | Zucherman et al. | |
| 2005/0143749 | A1* | 6/2005 | Zalenski | A61F 2/4611 606/99 |
| 2005/0197706 | A1 | 9/2005 | Hovorka et al. | |
| 2005/0209698 | A1* | 9/2005 | Gordon | A61B 17/7005 623/17.15 |
| 2005/0273171 | A1 | 12/2005 | Gordon et al. | |
| 2005/0283244 | A1 | 12/2005 | Gordon et al. | |
| 2006/0025777 | A1 | 2/2006 | Weber | |
| 2006/0064107 | A1* | 3/2006 | Bertagnoli | A61F 2/4611 606/99 |
| 2006/0116769 | A1* | 6/2006 | Marnay | A61F 2/4425 623/17.15 |
| 2006/0287728 | A1* | 12/2006 | Mokhtar | A61F 2/4425 623/17.14 |
| 2008/0109005 | A1* | 5/2008 | Trudeau | A61F 2/4425 606/99 |
| 2010/0023019 | A1* | 1/2010 | Fuhrer | A61F 2/4611 606/99 |
| 2010/0331988 | A1* | 12/2010 | Marnay | A61F 2/4425 623/17.16 |
| 2011/0112644 | A1* | 5/2011 | Zilberstein | A61B 17/7079 623/17.15 |
| 2015/0245924 | A1* | 9/2015 | Fuhrer | A61F 2/4611 623/17.16 |

* cited by examiner

PROSTHESIS HOLDER AND APPLICATION THEREOF

The present invention relates to prosthesis holders for discs and applications thereof.

Pathologies of the spinal column are increasingly treated by so-called "non-fusion" techniques and in particular by the implantation of disc prostheses.

These prostheses appear to produce good results.

However, their implantation is a serious and sometimes difficult operation. In fact, the ease and precision of the implantation play a predominant role in the final result, almost as much as the qualities of the disc prostheses themselves.

In fact, the position of the prosthesis in the disc space must be perfect in order to guarantee correct functioning. The surgeon verifies the position of the prosthesis during the surgical intervention using X-rays.

A disc prosthesis is a small object which is difficult to handle (of the order of one cm for its largest dimension and a few mm for its thickness). As a result its fitting utilizes a separate instrument called a prosthesis holder or insertion tool. This instrument provided with a handle is firmly fixed to the prosthesis in order to allow the surgeon to handle the latter with force. After fitting of the prosthesis, it must be able to be withdrawn and the prosthesis left in place.

At present, these instruments are often complicated. In particular, the mounting of the prosthesis on the prosthesis holder can prove difficult. Furthermore, these prosthesis holders are made of radio-opaque materials, which does not facilitate the X-ray visualization of the position of the prosthesis.

Certain prosthesis holders such as Cervidisc prosthesis from Scient'X or the Prestige prosthesis from Medtronics, form a clamp which will grip the prosthesis. When the prosthesis is installed in the correct position, it is released by loosing it from the clamp or pulling on the handle.

These instruments work well, However, the mounting of the prosthesis on its prosthesis holder is difficult and must be carried during the intervention by the surgeon or competent nursing staff. This represents a loss of time and risks of failure. Furthermore these instruments are radio-opaque, generally they are metallic. When the prosthesis is in place, the surgeon checks its position (often in profile) to see whether it is suitable or whether it must still be moved (for example impacted more). This is done by X-rays. It is therefore very difficult for the surgeon to distinguish between the prosthesis and the prosthesis holder; in particular, the surgeon has difficulty in visualizing the position of the front face of the prosthesis which is in contact with the prosthesis holder.

Moreover, whatever the existing systems (Maverick prostheses from Medtronics, Mobi-c from LDR, Prodisc from Synthes), the disconnection of the prosthesis holder from the prosthesis does not guarantee the stability of the implant in the disc space. In fact, the surgeon loosens the prosthesis holder then withdraws it. Therefore, when it is loosened it can easily be freed even if the prosthesis is not very stable in the space.

Furthermore, the disc prostheses being constituted by at least two parts which are mobile in relation to each other, it is not easy to fit these prostheses onto their prosthesis holder during the intervention in the operating suite (This is the case in particular for the Prodisc (Synthes), or Prestige (Medtronics), or Cervidisc prostheses (Scient'X).

The purpose of the invention is to remedy the drawbacks of the above prosthesis holder by proposing a prosthesis holder made of radiolucent material intended to be fixed on the one hand to the prosthesis by a clamp system and having a reversible coupling element with a handle such as a threaded or other hole on the other side.

After lengthy research the Applicant has developed a prosthesis holder which in particular does not interfere with the locating of the prosthesis, is easy to withdraw, and can also make it possible to verify the stability of the prosthesis. Furthermore, the coupling to the prosthesis which is carried out in the operating suite is very easy (simple screwing for example).

This is why a subject of the present application is a prosthesis holder for a disc prosthesis characterized in that it is made of radiolucent material, in that it comprises, on one side an element for coupling to a handle and on the other side, an element for reversible coupling to a disc prosthesis, in that the reversible coupling element is arranged in order to allow decoupling by simple traction exerted perpendicularly to a spinal column when the disc prosthesis is stable between two vertebrae and in that the retention force of the reversible coupling element on the disc prosthesis is adjusted so as not to allow decoupling by simple traction when the disc prosthesis is not stable between the two vertebrae.

Thus, when the disc prosthesis has been correctly impacted between two vertebrae and stability is correct, the decoupling occurs by simple traction. If on the other hand the disc prosthesis has not been correctly impacted or if the size of the prosthesis is chosen incorrectly (too small) the prosthesis is not stable, in this case, during the traction exerted by the surgeon, withdrawal of the disc prosthesis occurs and the surgeon understands that the disc prosthesis has not been correctly impacted or that its size is not suited to the disc space in question.

In the present application and in the remainder of the text, the term "reversible coupling" denotes a coupling which can be followed by a decoupling, in particular without using a tool.

The element for reversible coupling of the prosthesis holder to a disc prosthesis can take numerous forms. Preferably it comprises a follower device of a cam provided on the prosthesis, said follower device being elastically mounted on the prosthesis holder.

For example, the follower device is a bulge provided on U-shaped arms of the prosthesis holder (forming a fork), said arms being arranged in order to grip a prosthesis and said bulge being directed towards the inside of the U. Preferably the bulge is provided towards the end of the U-shaped arms. During the coupling, the follower device is guided for example by a groove or rib constituting the start of the cam then this groove or rib becomes hollow and the follower device (the bulge) will be housed in the recess formed in order to hold the prosthesis firmly.

Preferably a follower device is provided on each arm, in particular in a symmetrical position with respect to the direction of withdrawal.

Advantageously, four follower devices are provided.

In the example above, the depth of the cam hollow, the length, the thickness of the arms carrying the follower device as well as their geometry (profile in cross section in particular), and the material constituting the prosthesis holder determine the retention force of the reversible coupling element on the disc prosthesis. A person skilled in the art can, with a few simple experiments, determine the parameters necessary in order to obtain the desired retention force.

For a prosthesis intended for the cervical region, the retention force, necessary for disengagement, can be from 6 to 30 Newtons, preferably from 8 to 25 N, in particular from 9 to 20 N, quite particularly from 10 to 15 N.

For a prosthesis intended for the lumbar region, the retention force, necessary for disengagement, can be from 8 to 50 Newtons, preferably from 10 to 40 N, in particular from 12 to 30 N, quite particularly from 15 to 25 N.

A person skilled in the art understands that the bulges can be placed at various locations on the prosthesis holder as long as they are elastically mounted and corresponding recesses are provided on the prosthesis. Similarly, the bulges can be placed on the prosthesis and the recesses on the prosthesis holder.

The element for reversible coupling of the prosthesis holder to a disc prosthesis can also comprise studs, preferably cylindrical in shape, intended to be fitted into corresponding holes provided for this purpose in the prosthesis. The studs can be scored and slightly open in order to be fitted with force and to hold the prosthesis by adhesion, a minimum effort also being necessary in order to achieve decoupling.

Lateral friction surfaces of a fork-shaped prosthesis holder and of the prosthesis can also be practically parallel but slightly trapezoidal (for example with a relative inclination at an angle of 0.5 to 1°, the shorter base being towards the opening of the fork. A web can connect the branches of a fork-shaped prosthesis holder and a bulge or a recess can be provided on the webbed part.

A person skilled in the art can effortlessly understand when the term "one" signifies "at least one". For example when it says that the reversible coupling element of the prosthesis holder for a disc prosthesis can comprise "a follower device" of a cam provided on the prosthesis, "at least one follower device" is meant.

Under preferential conditions for implementation of the invention, the above prosthesis holder comprises a separate handle and retaining part as well as a system for the reversible coupling of the handle to the retaining part.

The handle allows the surgeon to grasp the prosthesis holder, for both insertion and impaction of the prosthesis and for decoupling and verification of the correct insertion thereof.

The handle can be coupled to the retaining part by any means well known to a person skilled in the art. There can be mentioned for example screw-and-thread devices, bayonet, clip devices etc.

Under preferential conditions for implementation of the invention, the above prosthesis holder comprises two arms forming a U-shaped clamp. Each of the two arms preferably comprises a bulge, said bulge being directed towards the inside of the U.

Under other preferential conditions for implementation of the invention, the above prosthesis holder has as a maximum the same width as the disc prosthesis for which it is intended.

Under yet other preferential conditions for implementation of the invention, the above prosthesis holder has a length, in the direction of the handle, preferably less than 10 cm, in particular less than 5 cm, particularly less than 3 cm, quite particularly less than 2 cm. For a prosthesis intended for the cervical region it has a width preferably of 1 to 3 cm, in particular of 1.2 to 2 cm, particularly of 1.3 to 1.9 cm, quite particularly of approximately 1.5 cm. For a prosthesis intended for the lumbar region it has a width preferably of 2 to 6 cm, in particular of 3 to 5 cm, particularly of 3 to 4 cm, quite particularly of approximately 3.5 cm.

Under yet other preferential conditions for implementation, the prosthesis holder of the invention has as a maximum the same height as the disc prosthesis for which it is intended. In particular it has as a maximum the same height and as a maximum the same width as the disc prosthesis for which it is intended.

The prosthesis holder of the invention is radiolucent. It is for example made of thermoplastic resin. The thermoplastic resin is for example high molecular weight polythene, PEEK loaded with glass or carbon fibres or pure, polyphenyl sulphones marketed under the name of Radel® and preferably acetal (thermoplastic homopolymer acetal resin which is reinforced or not reinforced). It can also be made of two or more two different materials. In this case, at least the major part serving to grasp the prosthesis and in contact with said prosthesis is advantageously radiolucent in order to make it possible to visualize the prosthesis in the disc space, whilst the remainder of the prosthesis holder is or is not made of radiolucent material.

The handle can be made of the same materials as the prosthesis holder, or of a different material, for example a metal such as stainless steel which is perfectly suitable.

The prosthesis holder which is the subject of the present invention possesses very useful qualities.

The fork being radiolucent, it is easy to visualize the prosthesis in the disc space. Furthermore, given its design, simple traction is sufficient to detach it from the prosthesis. This also has the advantage of verifying the stability of the prosthesis, in fact during traction, if the prosthesis remains connected to the prosthesis holder, it can be considered that its primary stability in the disc space was insufficient and another, larger size must generally be chosen.

They make it possible to hold together the different parts of a disc prosthesis during the intervention. They also have a reduced space requirement since their height can be less than that of the disc prosthesis and, similarly, their width can be less than that of said disc prosthesis.

It is also possible to have a prosthesis already fitted to the prosthesis holder in the factory. The mounting of the prosthesis holder thus comes down to screwing a rod into the threaded hole provided for this purpose. This operation is obviously straightforward.

A subject of the present application is therefore also an assembly (or kit) comprising a prosthesis holder and a prosthesis, preferably pre-mounted as well as, in particular, a handle. Preferentially, the various elements of the assembly are sterile and particularly sterile during packaging. The handle may not be sterile.

The arrangement in two parts of the prosthesis holder additionally makes it possible to avoid handling the implant which poses a risk of contamination. As the prosthesis is mounted on its prosthesis holder in the factory, it is even possible to mount the handle on the prosthesis holder without ever touching the prosthesis, this is the so-called "no touch" technique, i.e. nothing is touched, which is safest as regards asepsis.

These properties and qualities are illustrated hereafter in the figures. They justify the use of the prosthesis holders described above, in the fitting of disc prostheses between two vertebrae.

A subject of the present application is therefore also a method for fitting a disc prosthesis between two vertebrae in which a disc prosthesis is placed between two vertebrae using a prosthesis holder described above.

A subject of the present application is also method for choosing a disc prosthesis to be inserted between two vertebrae, in which a disc prosthesis is placed between two vertebrae using a prosthesis holder described above, traction is exerted on the prosthesis holder and it is observed whether the disc prosthesis remains in place or comes out with the prosthesis holder.

The preferential conditions for utilization of the prosthesis holders described above also apply to the other subjects of the invention referred to above, in particular to the assemblies comprising an above prosthesis holder and a disc prosthesis.

The invention will be better understood by referring to the attached drawings in which FIG. 1 shows a perspective view of a disc prosthesis constituted by at least two parts which are mobile in relation to each other, with its parts moved apart from each other.

The prosthesis 2 comprises an upper plate and a lower plate, approximately square in shape with rounded corners viewed from above. Each plate of the prosthesis 1 has a size of approximately 1.5 cm by 1.3 cm in this representation. The lower plate comprises a recess in which a dome 25 is housed. The upper plate comprises a concave recess the shape of which corresponds to that of the dome.

Figure 1:
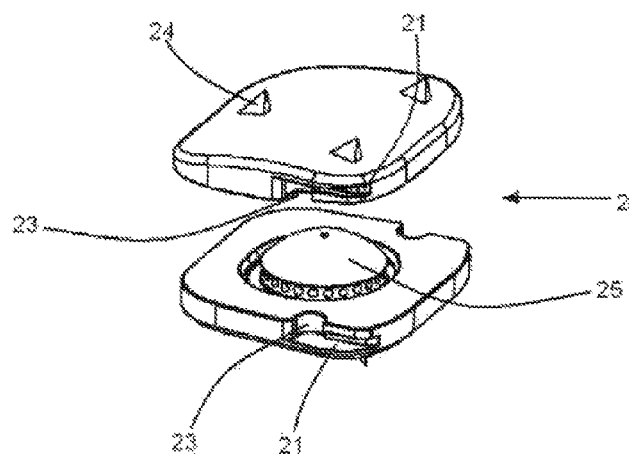
FIG. 1 shows a disc prosthesis constituted by at least two parts which are mobile in relation to each other, with its pieces moved apart from each other.
Figure 2:
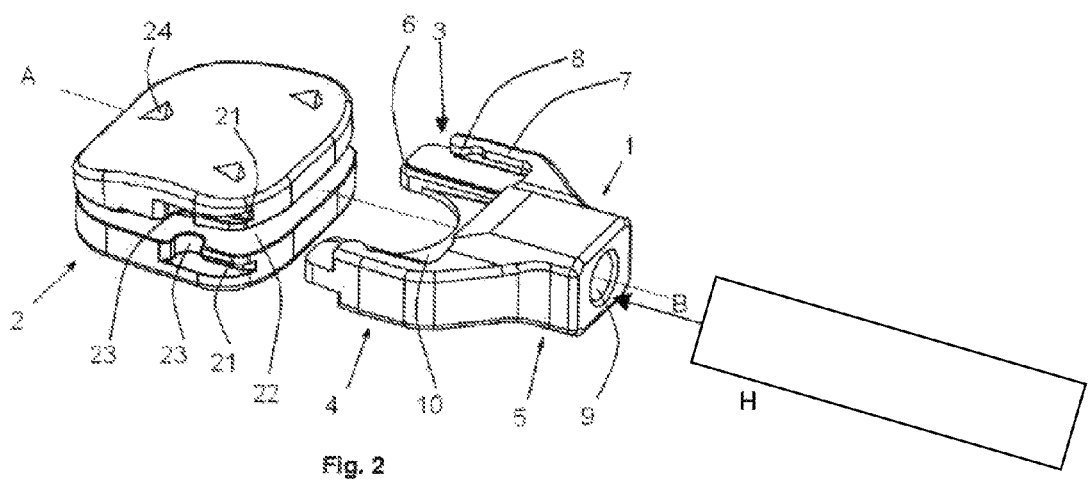
FIG. 2 shows a perspective view of a disc prosthesis holder as well as the corresponding prosthesis, separated.

The prosthesis 2 comprises hollowed out elements complementary to raised elements of the corresponding prosthesis holder of FIG. 2. Each plate comprises in particular along two opposite sides, grooves 21 forming a cam. Recesses 23, four in number, two on the left and two on the right of the prosthesis i.e. two per plate, are intended to receive the bulges 8 of the prosthesis holder. The dimensions of these elements are suited to those of the corresponding elements of the prosthesis holder.

The prosthesis 2 comprises, above and below, pointed elements 24 which allow the anchoring of the prosthesis after impaction.

FIG. 2 shows a disc prosthesis holder 1 as well as the corresponding prosthesis 2, separated. The prosthesis holder 1 is shown here without its handle. It has a general U-shaped fork appearance comprising two branches 3, 4 and a central part 5. Each of the branches comprises three ribs, a central rib 6, two secondary ribs 7 (only one per branch is visible in the figure). The central rib 6 with a significant thickness (from 1 to 5 mm according to the size of the prosthesis and its intended cervical or lumber region) serves as a main guide and gives solidity to the assembly, but does not allow the reversible coupling according to the invention. This is conferred by the secondary ribs 7 (with a thickness of approximately 0.4 to 3 mm) which comprise at their end a bulge 8 projecting towards the inside of the fork. This bulge 8 serves as a follower device. The bulges 8 are elastically mounted thanks to the geometry (profile in cross section in particular), and with the material constituting the prosthesis holder 1 here made of acetal, allowing the two arms to be moved apart from each other.

The cooperation of the ribs of the prosthesis holder 1 and the prosthesis 2 prevent the moving apart of the parts of the prosthesis 2 and the cooperation of the bulges 8 and recesses 23, combined with the cooperation of the dome 25 with the concavity of the upper part of the prosthesis 2, avoids the pieces of the prosthesis 2 sliding on one another, in order to firmly couple the two parts of the prosthesis 2.

In its central part 5, the prosthesis holder 2 comprises a threaded hole 9 into which a handle H can he screwed.

A web 10 connects the two arms 3 and 4 for good rigidity.

The prosthesis holder 1 has a height slightly less than that of the disc prosthesis 2. It has a length, in the direction of the handle, of approximately 1.5 cm, a width of approximately 1.5 cm and a height of approximately 6 mm in this representation.

The prosthesis 2 is here shown with the two plates moved together, the dome 25 in contact with the concave recess in the upper plate.

The prosthesis 2 comprises hollowed-out elements complementary to raised elements of the prosthesis holder and comprises in particular grooves 21 forming a cam which follows the bulge 8 during the coupling. The web 10 is housed in the space 22 between the upper plate of the prosthesis and the lower plate. Recesses 23, four in number, two on the left and two on the right of the prosthesis are intended to receive the bulges 8 of the prosthesis holder. The dimensions of these elements are suited to those of the corresponding elements of the prosthesis holder.

The prosthesis 2 comprises, above and below, pointed elements 24 which allow the anchoring of the prosthesis after impaction.

Figure 3:
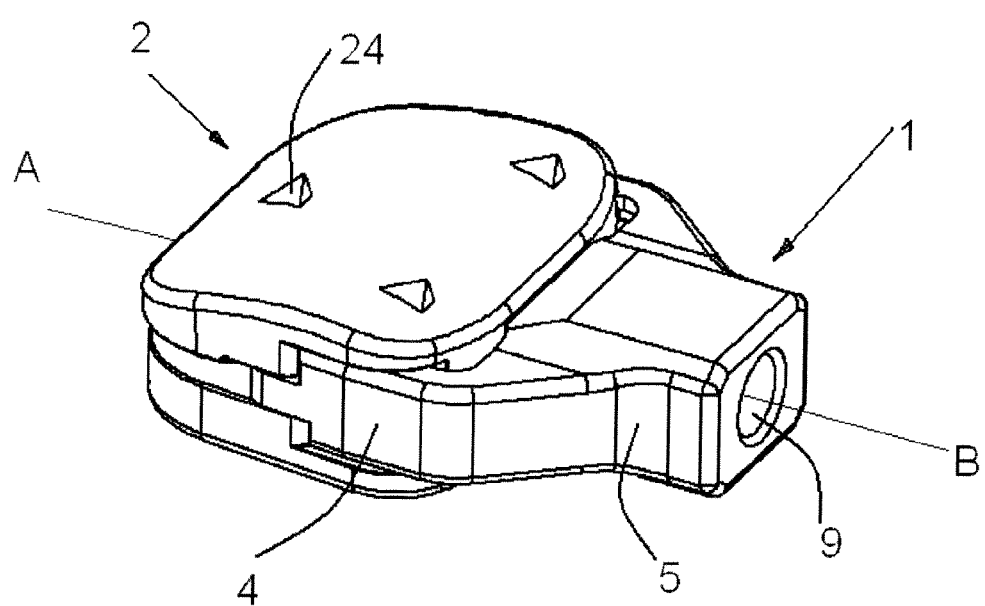
FIG. 3 shows a perspective view of a disc prosthesis holder as well as the corresponding prosthesis, pre-mounted.

During the coupling, shown in FIG. 3, the secondary ribs 7 are inserted into the grooves 21 serving as corresponding cams. In abutment, the bulges 8 are engaged in the recesses 23 so as to firmly couple the two parts of the prosthesis 2. A person skilled in the art understands, on examining the figures, that the bulges 8 can be placed at various locations on the prosthesis holder so long as they are elastically mounted and corresponding recesses 23 are provided on the prosthesis. Similarly, the bulges 8 can be placed on the prosthesis and the recesses 23 on the prosthesis holder.

The prosthesis 1 can be supplied with its prosthesis holder 2 already fitted in the factory as shown in FIG. 3. The final mounting of the prosthesis holder is thus limited to screwing a sleeve into the threaded hole 9 provided in its central part 5.

The depth of the hollow 23 of the grooves 21, the length, the thickness of the arms 3, 4 carrying the follower device as well as their geometry (profile in cross section in particular), and the material constituting the prosthesis holder 1 determine the retention force of the prosthesis holder on the prosthesis.

In order to withdraw the prosthesis holder 1 with a view to leaving the prosthesis 2 in place, and to verify the satisfactory stability of the latter, it is sufficient to pull on the handle in the direction AB. If the bulges 8 become disengaged from the recesses 23 leaving the prosthesis in place, this signifies that the latter is satisfactorily stable. The parts of the prosthesis are released and the plates can be moved in relation to each other, according to the ball joint provided by the dome.

FIG. 3 also shows that the use of ribs (or elongated slots for the female part) for coupling the two parts of the prosthesis 2 by means of the prosthesis holder 1 makes it possible to appreciably reduce the space requirement of the assembly. The prosthesis holder 1 in fact has the same width as the disc prosthesis 2 as can be clearly observed in the figure. It also has the same height as the disc prosthesis 2. A reduced space requirement is particularly useful as regards surgery.

The invention claimed is:

1. A method of fitting a disc prosthesis between two vertebrae of a spinal column, comprising the steps of:

a) selecting a disc prosthesis of a size intended to fit in stable manner between two vertebrae of the spinal column, a prosthesis holder of radiolucent material configured for reversibly coupling to the disc prosthesis, and a sleeve or handle for grasping the prosthesis holder, the disc prosthesis comprising at least two parts which are mobile in relation to each other, the prosthesis holder comprising at a first end an element for coupling the sleeve or handle to the prosthesis holder and at a second end opposing the first end a reversible coupling element comprising a U-shaped fork with two arms for reversibly coupling to the disc prosthesis by a retention force, the reversible coupling element being configured such that traction exerted perpendicularly to the spinal column is sufficient to overcome the retention force and allows decoupling of the prosthesis holder from the disc prosthesis when the disc prosthesis is stable between two vertebrae, the reversible coupling element being able to provide coupling and decoupling from the disc prosthesis without a tool, other than the sleeve or the handle for grasping the prosthesis holder, and the retention force is sufficient to firmly couple the mobile parts of the disc prosthesis, the retention force being adjusted so as not to allow decoupling by traction exerted perpendicularly to the spinal column when the disc prosthesis is not stable between the two vertebrae;

b) positioning the disc prosthesis between the two vertebrae of the spinal column using the prosthesis holder, the disc prosthesis mobile parts being reversibly coupled to the first end of the prosthesis holder and the sleeve or handle being coupled to the second end of the prosthesis holder;

c) verifying that the disc prosthesis is stable between the two vertebrae by pulling the sleeve or handle, the disc prosthesis being stable if the prosthesis holder is decoupled, without a tool, other than the sleeve or the handle for grasping the prosthesis holder, from the disc prosthesis as the handle is pulled, and the disc prosthesis being unstable if the disc prosthesis remains coupled to the prosthesis holder as the handle is pulled, wherein for an unstable disc prosthesis steps b) and c) are repeated until the disc prosthesis is stable between the two vertebrae.

2. The method according to claim 1, wherein, the disc prosthesis comprises a pair of ribs or grooves on the mobile parts, the prosthesis holder comprises a pair of grooves or ribs on each arm of the reversible coupling element that are complementary to said pair of ribs or grooves on the mobile parts, and the disc prosthesis is stable if the grooves or ribs from the prosthesis holder are decoupled from the complementary ribs or grooves of the disc prosthesis as the handle is pulled.

3. The method of claim 2, wherein, the mobile parts of the disc prosthesis comprise an upper plate and. a lower plate which are mobile in relation to each other, wherein each plate comprises a pair of grooves and a pair of recesses, and each groove and each recess are located on opposing sides of each plate, each arm of reversible coupling element of the prosthesis holder comprises a pair of parallel ribs extending towards a distal end of each arm, each rib having a bulge located closer to the distal end than the element for coupling to the handle, each rib is complementary to and arranged to cooperate with one of said grooves of the two plates of the disc prosthesis and each bulge is complementary to and arranged to cooperate with one of said recesses of the two plates of the disc prosthesis to provide reversible coupling between the two plates of the disc prosthesis and said reversible coupling element, and the disc prosthesis is stable if the ribs and bulges from the prosthesis holder are decoupled from the complementary grooves and recess of the disc prosthesis as the handle is pulled.

4. The method according to claim 1, wherein in step a) the disc prosthesis, the prosthesis holder and the handle are selected in a pre-assembled form such that the disc prosthesis is reversibly coupled with the prosthesis holder, and the handle Is coupled with the prosthesis holder.

5. The method according to claim 1, wherein in step a) the handle is integral with the prosthesis holder.

6. The method according to claim 5, wherein in step a) the disc prosthesis, the prosthesis holder and handle integral with the prosthesis holder are selected in a pre-assembled form such that the disc prosthesis is reversibly coupled with the prosthesis holder.

7. The method according to claim 1, wherein the sleeve or handle is configured for being reversibly coupled to the prosthesis holder, and the prosthesis holder comprises a retaining part and a system for the reversible coupling of the sleeve or handle to the retaining part.

8. The method according to claim 1, wherein the prosthesis holder is made of thermoplastic resin.

9. A method for determining whether a disc prosthesis is a correct size to be stable between two vertebrae of a spinal column, comprising the steps of:

a) selecting a disc prosthesis of a size that fits between two vertebrae of the spinal column, a prosthesis holder of radiolucent material configured for reversibly coupling to the disc prosthesis and a sleeve or handle for grasping the prosthesis holder, the disc prosthesis comprising at least two parts which are mobile in relation to each other, the prosthesis holder comprising at a first end an element for coupling the sleeve or handle to the prosthesis holder and at a second end opposing the first end a reversible coupling element comprising a U-shaped fork with two arms for reversibly coupling to the disc prosthesis by a retention force, the reversible coupling element being configured such that traction exerted perpendicularly to the spinal column is sufficient to overcome the retention force and allows decoupling of the prosthesis holder from the disc prosthesis when the disc prosthesis is stable between two vertebrae, the reversible coupling element being able to provide coupling and decoupling from the disc prosthesis without a tool, other than the sleeve or the handle for grasping the prosthesis holder, and the retention force is sufficient to firmly couple the mobile parts of the disc prosthesis, the retention force being adjustable so as not to allow decoupling by traction exerted perpendicularly to the spinal column when the disc prosthesis is not stable between the two vertebrae;

b) positioning the disc prosthesis between the two vertebrae of the spinal column using the prosthesis holder, the disc prosthesis mobile parts being reversibly coupled to the first end of the prosthesis holder and the sleeve or handle being coupled to the second end of the prosthesis holder;

c) pulling the sleeve or handle to determine whether the disc prosthesis is a correct size to be stable between two vertebrae, the disc prosthesis being the correct size if the prosthesis holder is decoupled from the disc prosthesis as the sleeve or handle is pulled, and the disc prosthesis being an incorrect size to be stable between the two vertebrae if the disc prosthesis remains coupled to the prosthesis holder as the sleeve or handle is pulled, wherein for a disc prosthesis that is an incorrect size, steps b) and c) are repeated until the prosthesis holder is decoupled from the disc prosthesis as the sleeve or handle is pulled or the disc prosthesis is designated as having an incorrect size to be stable between the two vertebrae, and wherein when a disc prosthesis is designated as having an incorrect size, steps a), b) and c) are repeated for a disc prosthesis that is a larger size than the disc prosthesis having an incorrect size.

10. The method according to claim 9, wherein, the disc prosthesis comprises a pair of ribs or grooves on the mobile parts, the prosthesis holder comprises a pair of grooves or ribs on each arm of the reversible coupling element that are complementary to said pair of ribs or grooves on the mobile parts, and the disc prosthesis is the correct size if the grooves or ribs from the prosthesis holder are decoupled from the complementary ribs or grooves of the disc prosthesis as the sleeve or handle is pulled.

11. The method of claim 10, wherein, the mobile parts of the disc prosthesis comprise an upper plate and a lower plate which are mobile in relation to each other, wherein each plate comprises a pair of grooves and a pair of recesses, and each groove and each recess are located on opposing sides of each plate, each arm of reversible coupling element of the prosthesis holder comprises a pair of parallel ribs extending towards a distal end of each arm, each rib having a bulge located closer to the distal end than the element for coupling to the sleeve or handle, each rib is complementary to and arranged to cooperate with one of said grooves of the two plates of the disc prosthesis and each bulge is complementary to and arranged to cooperate with one of said recesses of the two plates of the disc prosthesis to provide reversible coupling between the two plates of the disc prosthesis and said reversible coupling element, and the disc prosthesis is the correct size if the ribs and bulges from the prosthesis holder are decoupled from the complementary grooves and recess of the disc prosthesis as the sleeve or handle is pulled.

12. The method according to claim 9, wherein in step a) the disc prosthesis, the prosthesis holder and the sleeve or handle are selected in a pre-assembled form such that the disc prosthesis is reversibly coupled with the prosthesis holder, and the sleeve or handle is coupled with the prosthesis holder.

13. The method according to claim 9, wherein in step a) the sleeve or handle is integral with the prosthesis holder.

14. The method according to claim 13, wherein in step a) the disc prosthesis, the prosthesis holder and the sleeve or handle integral with the prosthesis holder are selected in a pre-assembled form such that the disc prosthesis is reversibly coupled with the prosthesis holder.

15. The method. according to claim 9, wherein the sleeve or handle is configured for being reversibly coupled to the prosthesis holder, and the prosthesis holder comprises a retaining part and a system for the reversible coupling of the sleeve or handle to the retaining part.

16. The method according to claim 9, wherein the prosthesis holder is made of thermoplastic resin.

* * * * *